United States Patent [19]
Hampson et al.

[11] Patent Number: 5,589,339
[45] Date of Patent: Dec. 31, 1996

[54] SUBTRACTION HYBRIDIZATION

[75] Inventors: Ian N. Hampson; Lynne Pope, both of Heywood; John Butler, Stockport, all of United Kingdom

[73] Assignee: Amersham International PLC, Bucks, United Kingdom

[21] Appl. No.: 467,716

[22] Filed: Jun. 6, 1995

Related U.S. Application Data

[63] Continuation of Ser. No. 43,744, Apr. 7, 1993.
[51] Int. Cl.$^6$ .............................. C12Q 1/68; C12P 19/34
[52] U.S. Cl. .............................................. 435/6; 435/91.2
[58] Field of Search ........................... 435/6, 91.2

[56] References Cited

U.S. PATENT DOCUMENTS

| | | |
|---|---|---|
| 4,599,303 | 7/1986 | Yabusaki et al. . |
| 5,032,502 | 7/1991 | Stodolsky ................................... 435/6 |
| 5,221,608 | 6/1993 | Cimino et al. ............................ 435/6 |

OTHER PUBLICATIONS

Travis et al; Phenol emulsion–enhanced DNA–driven subtractive cDNA cloning: Isolation of low–abundance monkey cortex-specific mRNAs; Proc. Natl. Acad. Sci. USA; Mar. 1988; pp. 1696–1700.
Manufacturer's Leaflet entitled "Sequenase Random Primed DNA Labeling Kit"; United States Biochemical; pp. 101–104.
Scott et al; Activation of Mouse Genes In Transformed Cells; Cell; vol. 34; 1983; pp. 557–567.
Duguid et al; Isolation of cDNAs of scrapie–modulated RNAs by subtractive hybridization of a cDNA library; Proc. Natl. Acad. Sci. USA; vol. 85; 1988; pp. 5738–5742.
Wang et al; A gene expression screen; Proc. Natl. Acad. Sci., USA; vol. 88, 1991; pp. 11505–11509.
Feinberg et al; Addendum "A Technique for Radiolabeling DNA Restriction Endonuclease Fragments to High Specific Activity"; vol. 132, No. 1; 1983; pp. 6–13.
Espelund et al; A simple method for generating single–stranded DNA probes labeled to high activities; Nucleic Acids Research, vol. 18, No. 20; 1990.
Matthews et al; Review Analytical Strategies for the Use of DNA Probes. Anal. Biochem. (1988) 169: 1–25.
Palazzolo et al; A family of lambdaphage cDNA cloning vectors, SWAJ, allowing the amplification of RNA sequences Gene (1987) 52: 197–206.
Hartley et al; DNA Cross–linking and Sequence Selectivity of Aziridinylbenzoquinones; A Unique Reaction at 5'–GC–3' Sequences . . . Biochemistry (1991) 30: 11719–11724.
Hampson et al., Chemical crosslinking subtraction (CCLS); a new method for the generation of subtractive hybridization probes Nucl. Acids Res (1992) 20: 2899.
Hartley et al. (1990) *Biochemistry* 30:11719–11724.
Birkenbach et al. (1989) J. Virology 63:4079–84.
Timberlake (1980) Dev. Biol. 78:497–510.
Sive and St. John (1988) Nucleic Acids Res. 16:10937.
Kuze et al. (1989) Nucleic Acids Res. 17:807.
Lee et al. (1992) Biochemistry 31:3019–25.
Sargent (1987) Methods in Enzymology 152:423–432.
Rubenstein et al. (1990) Nucleic Acids Res. 18:4833–42.
Hedrick et al. (1984) Nature 308:149–153.

*Primary Examiner*—W. Gary Jones
*Assistant Examiner*—Amy Atzel
*Attorney, Agent, or Firm*—Cushman Darby & Cushman LLP

[57] ABSTRACT

A novel process is disclosed utilizing a subtraction hybridization technique for producing DNA hybridization probes of high specific activity or cDNA subtraction libraries, useful in connection with the cloning of differentially expressed genes. A preparation of single stranded cDNA derived from transcript mRNA of a target cell source is subjected to subtraction hybridization using excess single stranded "driver" nucleic acid from a reference cell source so that all the cDNA having a nucleotide sequence complementary to transcript mRNA of the reference cell source is subtracted by annealing with the "driver" nucleic acid to form duplex molecules. The strands of these duplex molecules are then chemically cross-linked by treatment with an aziridinylbenzoquinone interstrand cross-linking agent, and the remaining unsubtracted single stranded unique cDNA derived solely from the target cell source is processed in the presence of the chemically cross-linked duplex molecules to provide labelled probe material or a subtraction cDNA library, using random priming and a DNA polymerase lacking exonuclease activity and inactive with respect to the cross-linked duplex molecules.

17 Claims, 1 Drawing Sheet

O-6MMT-    -ACTIN

SUBTRACTION HYBRIDIZATION

This is a continuation of application Ser. No. 08/043,744, filed Apr. 7, 1993.

FIELD OF THE INVENTION

The present invention relates to the field of molecular biology and is particularly concerned with the technique known as subtraction hybridization. This is a technique often used in connection with methods for detecting and identifying differences in gene expression between related tissue cells, such as may perhaps arise in cells that have undergone some genetic modification. The technique can be especially useful for facilitating production of specific screening probes usable for example in conjunction with gene cloning procedures for isolating the gene sequences involved in such differential gene expression, and in preparing so-called subtraction libraries in which DNA derived from differentially expressed genes is enriched. The invention also specifically concerns a novel process using a subtraction hybridization method for producing labelled DNA hybridization probes of high specific label activity.

BACKGROUND OF THE INVENTION

Subtraction hybridization as commonly used in association with cloning of cDNA derived from mRNA extracted from particular cells that are under investigation is most useful, as already indicated, for developing or producing hybridization probes that can be utilised as screening agents to detect or locate DNA, in clone colonies or cDNA libraries for example, related to genes that are differentially expressed as compared with genes of other cells that exhibit different gene expression characteristics. This technique may, for example, be used in cancer research for comparing the gene products of tumour tissue cells with those of corresponding normal tissue cells in order to study the genetic changes that have occurred at the nucleic acid level. Probes obtained using this technique which are specific to DNA whose expression characteristics are modified by such genetic changes may be useful not only for carrying out genetic screening in connection with cDNA cloning, but also as diagnostic tools.

In a typical procedure for applying this technique of subtraction hybridization to investigate differences in the active genes of a certain sample of test or target cells, e.g. from tumour tissues, as compared with the active genes of a sample of reference cells, e.g. cells from corresponding normal tissue, total cell mRNA is extracted (using conventional methods) from both samples of cells. The mRNA in the extract from the test or target cells is then used in a conventional manner to synthesise corresponding single stranded cDNA using an appropriate primer and a reverse transcriptase in the presence of the necessary deoxynucleoside triphosphates, the template mRNA finally being degraded by alkaline hydrolysis to leave only the single stranded cDNA. In one particular version of the technique, especially relevant to the present invention, care is taken to avoid unwanted synthesis of any second strand cDNA in this initial stage. The single stranded cDNA thus derived from the mRNA expressed by the test or target cells is then mixed under hybridizing conditions with an excess quantity of the mRNA extract from the reference (normal) cells. The latter is herein generally termed the subtraction hybridization "driver" since it is this mRNA or other single stranded nucleic acid present in excess which "drives" the subtraction process. As a result, cDNA strands having common complementary sequences anneal with the mRNA strands to form mRNA/cDNA duplexes and are thus subtracted from the single stranded species present. The only single stranded DNA remaining is then the unique cDNA that is derived specifically from the mRNA produced by genes which are expressed solely by the test or target cells.

From this point onwards, to complete the subtraction process and use the single stranded unique cDNA, for example for producing labelled probes that may perhaps then be used for detecting or identifying corresponding cloned copies in a cDNA clone colony (labelling of such probes is frequently introduced by using labelled deoxynucleoside triphosphates in synthesis of the cDNA), it has hitherto generally been necessary first physically to separate out the common mRNA/cDNA duplexes, using for example hydroxyapatite (HAP) or (strept)avidin-biotin in a chromatographic separation method, after which one or more repeat rounds of the subtraction hybridization may be carried out to improve the extent of recovery of the desired product.

This same need physically to separate out the duplex molecules generated in the subtraction hybridization stage has moreover remained even in many variations or modifications that have been used or proposed in respect of the basic subtraction hybridization scheme outline above, for example variations or modifications in which cDNA derived from mRNA of both cell sources is first synthesized and possibly amplified by a cloning or polymerase chain reaction (PCR) procedure, followed by using one of the cDNA mixtures (after denaturation where the cDNA is doublestranded) as the "driver" for carrying out the subtraction hybridization. The known and published methods for separating out the duplex molecules from the single stranded unique cDNA product, such as the above-mentioned hydroxyapatite or (strept)avidin-biotin chromatographic separation methods, however, are not entirely satisfactory, often leading to incomplete separation of the duplexes and a significant loss of unique cDNA or potential probe material. Such defects can be especially serious when the genetic material of interest provides only mRNA transcripts at a low abundance. Also, these known methods usually involve a fairly complex procedure requiring considerable experimental manipulation throughout, and particularly in producing radiolabelled probes the handling of radioactive material throughout a number of different stages introduces additional complications and hazards.

SUMMARY OF THE INVENTION

Accordingly, it is an object of the present invention to provide an improved subtraction hybridization process which permits use of a simplified procedure and which can enable at least some of the disadvantages or problems associated with the methods hitherto known, such as the disadvantages or problems indicated above, to be overcome.

It is a further specific object of the invention to provide a novel procedure for carrying out a subtraction hybridization process which, for at least many end uses, requires no physical separation of the duplex molecules, generated during the subtraction hybridization stage, from the unique cDNA product.

It is a further object of at least some embodiments of the invention to provide an improved process for producing efficiently DNA hybridization probes of high specific activity from target tissue cells having genes that are differentially expressed as compared with the genes of reference tissue cells, effective even when the product of such differential gene expression is of low abundance.

It is yet another specific object of at least some embodiments of the invention to provide a subtraction hybridization process for producing DNA hybridization probes which enables multiple probes to be prepared from the same batch of subtracted material.

A yet further object of at least some embodiments of the invention is to provide an improved subtraction hybridization process for use in preparing subtraction cDNA libraries in connection with differential gene expression screening investigations.

These, and further objects and features of the invention, will become more clearly apparent from the description hereinafter contained.

The present invention provides basically a subtraction hybridization process in which the nucleotide strands of the duplex molecules generated in carrying out the subtraction hybridization are chemically cross-linked and stabilized without affecting remaining non-subtracted single stranded unique cDNA present in the reaction mixture, using for this purpose an aziridinylbenzoquinone interstrand cross-linking agent.

Thus, in applying the invention to a subtraction hybridization process wherein single stranded cDNA derived from transcript RNA of a target cell source is reacted under hybridizing conditions (through one or more cycles) with excess single stranded hybridization driver nucleic acid derived from transcript RNA of a reference source so as to cause substantially all said cDNA having a nucleotide sequence complementary to RNA that is common to both said sources to become bound in duplex molecules such that the only single stranded cDNA then remaining is that having a sequence complementary to transcript RNA that is specific to the target cell source, that is, unique cDNA derived solely from said target cell source, the reaction mixture is treated with an aziridinylbenzoquinone interstrand cross-linking agent effective selectively to chemically cross-link the nucleotide strands in the duplex molecules, thereby increasing the stability of these molecules, without affecting the remaining single stranded unique cDNA.

It has been found that after carrying out the subtraction hybridization process substantially as specified above, the non-subtracted single stranded unique cDNA that remains can then be subjected to a labelling operation without complications arising from the continued presence of the chemically cross-linked duplex molecules if a complementary DNA strand incorporating labelled nucleosides is synthesised from this non-subtracted single strand cDNA which provides a template, using a DNA polymerase which lacks exonuclease activity and which is inactive with respect to said duplex molecules. Upon termination of the labelling reaction, the double stranded product can then be denatured, for example by boiling, to release the single strand length or lengths of labelled DNA from the template strand, ready for use as a probe or probes. Consequently, the basic novel subtraction hybridization process is extendable to produce labelled DNA hybridization probes in a very convenient and advantageous manner.

DNA polymerases with the required characteristics specified above for the labelling operation are available commercially, such as for example that supplied under the Registered Trade Mark "Sequenase" by United States Biochemical of Cleveland, Ohio, U.S.A. which not only lacks exonuclease activity but is also unable to utilise RNA as a template for synthesis. The labelling method employed is preferably a random priming method using, in conjunction with the DNA polymerase, a random oligonucleotide primer mixture and the necessary deoxynucleoside triphosphates of which at least one species carries the labelling. Complete Random Primed DNA labelling kits suitable for this purpose, including the Sequenase$^{RTM}$ DNA polymerase and including a recommended protocol for use thereof, are also supplied by the same Company, United States Biochemical (Product No. 70150). In most cases, a radioactive label is preferred with a radioactive deoxynucleoside triphosphate being used in the labelling operation.

In carrying out the subtraction hybridization process in accordance with the invention, in order to ensure that substantially all the free cDNA derived from transcript RNA (or more specifically mRNA) common to both the target cell source and the reference source is hybridized and subtracted by the driver nucleic acid, the initial round of subtraction hybridization may be repeated if required one or more times, using each time a fresh quantity of the driver nucleic acid. Also, it will be appreciated that the final batch of subtracted material may, if desired, be divided into two or more portions, thereby enabling a corresponding multiple number of probe preparations to be made at different times, as and when required. Furthermore, since the labelling operation for producing probes is not carried out until after performing the subtraction hybridization, the reaction mixture containing the subtracted material can in any case be stored at a suitably low temperature so that, if desired, the labelling operation can be delayed and carried out later at such time that the probe is required for use. This is especially important when using radioactive labelling material as the amount of manipulation of radiolabelled DNA is reduced and the effects of decay in probe activity during the subtractive hybridization are eliminated.

Another major advantage arises from the fact that the main series of operations can generally all be carried out in the same single reaction vessel if desired.

The aziridinylbenzoquinone interstrand cross-linking agent used should be capable, under the conditions existing in the reaction mixture, of promoting cross-linking of substantially all the duplex molecules present, i.e. effectively 100% cross-linking, and should be capable of bonding to short but specific nucleotide sequences in DNA strands. Preferably, it is a compound of the formula

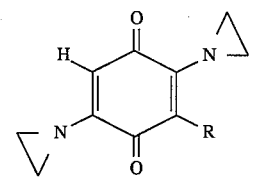

in which R is selected from H, alkyl, thiol, alcohol and halide. When R is alkyl, thiol or alcohol it is preferred that it should not contain more than six carbon atoms, the size of the group being limited by a need to avoid unduly impairing favourable physical properties such as solubility. Especially satisfactory cross-linking may be established when R is methyl, ethyl or propyl, or one of the corresponding lower alkyl thiols or alcohols. However, the most preferred compound is the symmetric compound 2,5-diaziridinyl-1,4-benzoquinone (DZQ) which, under reducing conditions (giving the reduced hydroquinone form) at neutral pH, was reported by J. A. Hartley et al, (1991) *Biochemistry*, 30, 11719–11724, as being able to produce 100% interstrand cross-linking, primarily between GC pairs in 5'-TGC-3' sequences, in DNA nucleic acid duplexes.

The subtraction hybridization process of the present invention can usefully be used, as hereinafter explained, where the single stranded hybridization driver nucleic acid is cDNA derived, via synthesis and denaturation of double stranded cDNA (amplified possibly by PCR), from mRNA of the reference source. However, in general the single stranded hybridization driver nucleic acid is preferably RNA provided directly, or through an RNA cloning amplification process (see later), by the mRNA of the reference source so that the duplex molecules produced on hybridization are in fact RNA/DNA duplexes. Somewhat unexpectedly, it has been found that the aziridinylbenzoquinone interstrand cross-linking agents referred to above are effective and can be used with both DNA/DNA duplexes and RNA/DNA duplexes, although a rather higher concentration is usually found to be required for use with a given concentration of RNA/DNA duplexes than is needed for use with a similar concentration of DNA/DNA duplexes in order to achieve the most satisfactory results.

According to a refinement or development of the basic process outlined above for producing probes, the labelling operation may alternatively be carried out while the unsubtracted unique cDNA and the cross-linked duplex molecules are all immobilised on a solid phase support instead of being free in the reaction mixture. Thus, in carrying out this modified version of the process, the first strand cDNA may be synthesized initially using a biotinylated primer, the subtraction hybridization and chemical interstrand cross-linking operations are carried out as before, and then, before labelling, a solid phase support material coated with avidin or streptavidin is introduced into the reaction mixture. Since all the cDNA, both the non-subtracted single stranded cDNA and the subtracted cDNA incorporated in the cross-linked duplex molecules, will carry biotin terminal groups which bind to the avidin or streptavidin of the solid support material, all the molecules containing such cDNA are effectively immobilised. It has been found that the previously described selective labelling operation of the unique cDNA, using for example the preferred random priming technique, can then still be carried out, without interference in respect of the cross-linked duplexes, while both molecular species remain bound in situ to the support. The temperature can then be raised by heating, e.g. to about 90° C., for a short time in order to denature the doublestranded DNA formed in the labelling operation, thus releasing the labelled strand or strands lengths providing the probe material while leaving the original unsubtracted unique cDNA template strand in place. After decanting or filtering off the solution containing this labelled single strand probe material, the labelling operation may thereafter be repeated as many times as desired in order to continue producing further probe material, all from the same cDNA template originating from a single batch of subtracted material.

A particularly convenient form of solid support for use in this modified version of the process is provided by magnetic beads or microspheres such as, for example, those which are commercially available already coated with streptavidin from Dynal Limited (UK) under the Trade Mark Dynabeads M-280 Streptavidin. Such magnetic beads can readily be manipulated within the reaction mixture by using external magnets, thereby considerably facilitating handling and filtering or separation operations.

This above-described modified version of the process in which cDNA from the target cell source is immobilised on a solid phase support through interaction between suitable binding groups such as biotin and complementary receptor material such as (strept)avidin is generally advantageous when the hybridization driver nucleic acid is an RNA derived from the reference source. It can be especially important, however, if in carrying out the invention it is desired to produce labelled DNA hybridization probes using cDNA derived from the reference source as the subtraction hybridization driver because in that case there arises an additional requirement to separate or distinguish the excess single stranded driver cDNA that remains after the subtraction hybridization from the unsubtracted unique single stranded cDNA, in order to permit the selective labelling of the latter. As will be appreciated, such separation can readily be achieved when all the unsubtracted unique single stranded cDNA is immobilised and bound to a solid support material, as above described, simply by decanting or filtering off the solution containing the residual excess driver cDNA before releasing the labelled probe material from the solid support, and preferably before even commencing to carry out the labelling operation. Alternatively, to achieve separation from the unsubtracted unique single stranded cDNA before labelling of the latter, a cDNA subtraction hybridization driver may itself carry the biotin binding group instead of the cDNA derived from the target cell source so that the solution which is decanted or filtered off then contains the unique single stranded cDNA ready for labelling whilst the excess single stranded driver cDNA (and cDNA duplexes) remains behind, immobilised on the solid support. This is not a preferred procedure, however, since there is a greater risk of excessive or unnecessary loss of probe material and the full benefits of the invention are unlikely to be fully realised.

In addition to the production of DNA hybridizing probes, the subtraction hybridization process of the present invention is also useful for preparing cDNA subtraction libraries, for example by using the single stranded unique cDNA product for cloning in suitable vectors and transformant host cells. For cloning, it will of course generally be necessary to convert this single stranded cDNA into a double stranded form, but this may be achieved by again carrying out a random priming operation, again using Sequenase$^{RTM}$, exactly as when producing probes except that no labelling need be incorporated and the double stranded product will not require to be denatured although it may need ligase treatment and also the addition of linkers to create suitable restriction sites for insertion and cloning in the chosen vector. Such cloning operations can still be carried out with in the presence of the chemically cross-linked RNA/DNA duplex molecules since (a) the latter, with the interstrand chemical cross-linking, would not be susceptible to cloning, and (b) the addition to a RNA/DNA duplex of restriction site linkers, necessary for insertion into the vector, would be very inefficient compared with addition to a DNA/DNA duplex. Alternatively, however, if the subtraction hybridization is carried out with the duplexes and unique single stranded cDNA immobilised on a solid phase support, as in the modification of the main process herein described, then after carrying out a first stage of random priming as in producing probes, using Sequenase$^{RTM}$ but without labelling, and denaturing to release the newly-synthesised single stranded DNA, the solution containing the latter may be decanted or filtered off. This solution can then be subjected to a further round of DNA synthesis using a DNA polymerase which, at this stage, may be either Sequenase$^{RTM}$ again or a Klenow fragment DNA polymerase in order to provide the required double stranded DNA for cloning.

BRIEF DESCRIPTION OF THE DRAWINGS

In the accompanying drawings.

DETAILED DESCRIPTION OF A PREFERRED EMBODIMENT OF THE INVENTION

Figure 1A:
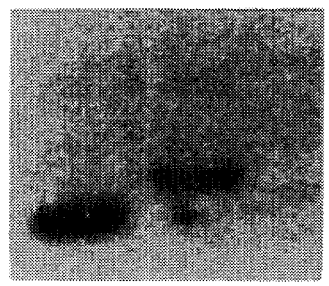
FIG. 1 comprises two panels marked "A" and "B" which represent reproductions of autoradiographs showing Southern blots carried out on samples (100 ng each) of α-actin and O⁶-MMT cDNA cloning vector inserts using probes made from equal amounts of cDNA derived from mitozolamide treated RJKO cells, the probe used in the case of panel "A" being a subtracted probe prepared as hereinafter described in accordance with the present invention and the probe used in the case of panel "B" being an unsubtracted probe.

By way of further description of the invention, and to illustrate the preferred manner of putting it into practice, a specific test example will now be more fully described.

EXAMPLE

This test example relates to preparation of a high specific activity radiolabelled DNA hybridization probe adapted for use in detecting and identifying expression of the $O^6$-methylguanine methyltransferase gene ($O^6$-MMT) in eukaryotic cells treated with the alkylating antitumour drug mitozolamide.

In this example, RJKO cells (a known Chinese hamster lung fibroblast cell line) were used which normally express RNA transcripts for the protein α-actin. As disclosed by Morten and Margison (1988) Carcinogenesis, 9, 45–49, treatment with mitozolamide induces in such RJKO cells expression also of the $O^6$-MMT gene, but the mRNA transcripts from the latter are in relatively low abundance as compared with those from the α-actin gene.

Materials Used

Other than standard laboratory reagents, these included:
RJKO cells kindly supplied by Dr. G. P. Margison (co-author of the above-mentioned paper);

"Superscript"™ reverse transcriptase (a ribonuclease H⁻ recombinant form of Moloney murine leukaemia virus reverse transcriptase) from Gibco BRL, Paisley, Scotland;

"Sequenase II"$^{RTM}$ T7 DNA polymerase from United States Biochemical (Cleveland, Ohio, U.S.A.);

2,5-diazaridinyl-1,4-benzoquinone (DZQ).

Preparation of DZQ

This compound is not readily available commercially, but methods of synthesis of DZQ and other aziridinylbenzoquinones have been previously described in various publications (see, for example, Chou, F., et al (1976) J. Med. Chem. 19, 1302., Dzielendziak, A., & Butler, J (1989) Synthesis, 643, Dzielendziak, A., et al, (1990) Cancer Res. 50, 2003 and Petersen, S., et al (1955) Angew. Chem. 67, 217). For the purpose of this example, a quantity of DZQ was synthesised as follows:

Sublimed benzoquinone (2.25 g) was suspended in tetrahydrofuran (20 ml) dried over molecular sieves (both compounds obtained from Aldrich Chemical Co. Ltd., Gillingham, Dorset, U.K.). Working in a fume cupboard and taking appropriate precautions to reduce toxicity and explosion hazards, 3 ml of aziridine (obtained from Serva Feinbiochemica GmbH & Co. KG, of P.O. Box No. 105260, Carl Benz Strasse 7, D-6900 Heidelberg, Germany) in dry tetrahydrofuran (5 ml) was then added to this suspension, and the reaction mixture was stirred for 20 minutes on ice, followed by filtering and drying under vacuum. The target product thus obtained was finally recrystallized by adding an excess of ethanol (dried over sodium metal). Yield of DZQ—at least 0.5 g.

Other analogues within the scope of the invention may be prepared by similar methods, using the appropriate benzoquinone derivative.

Culture and Treatment of RJKO cells and isolation of mRNA therefrom

The RJKO cells were cultured and one sample thereof was treated with the alkylating drug mitozolomide substantially as described by Morten and Margison in their above-mentioned paper of which the content is incorporated herein by reference. A second sample was left untreated to provide a control or reference cell source, the treated sample constituting the test or target cell source. Using conventional techniques, total RNA was extracted and purified from both cell samples by means of the cytoplasmic lysis method of Favoloro, J. R., Treisman, R. & Kamon, R. (see Methods in Enzmology (1980) 65, 718), and from this polyadenylated mRNA (Poly A⁺ mRNA) was selected and purified using oligo dT cellulose chromatography as described by Aviv, H. and Leder, P. (1974) Proc. Natl. Acad. Sci. USA 69, 1408. Again, the content of both the two above-mentioned papers are incorporated herein by reference. To ensure that the Poly A⁺ mRNA preparations were free of DNA, they were digested with DNase. This was accomplished by resuspending the RNA and DNase I buffer (0.1M sodium acetate, 5 mM magnesium sulphate, pH 5.0) in a volume of about 50 μl. 10 units of ribonuclease free DNase I (supplied by Boehringer Mannheim, Cat. No. 776785) was added and the mixture incubated for 15 minutes at 37° C. Following this the DNase I was inactivated by two extractions with phenol/chloroform (50:50) and the mRNA was precipitated with ethanol.

Procedure (a) Synthesis of first strand cDNA

Poly A⁺ mRNA, (3–5 μg), free of DNA, from the mitozolamide treated cells was processed to synthesize corresponding first strand cDNA copies using unlabelled deoxynucleoside triphosphates and "Superscript"™ reverse transcriptase in accordance with the manufacturer's recommended protocol. The choice of this particular reverse transcriptase enzyme, in preference to other avian or murine reverse transcriptase enzymes, was important because it is free of RNase H which degrades RNA in DNA/RNA hybrids and which, as a result of premature degradation of the parental mRNA template strand under synthesizing conditions, could lead to miscellaneous priming of exposed first strand cDNA and hence excessive second strand cDNA synthesis. In order to carry out the method of the present invention satisfactorily, wherein originally isolated mRNA is used as the driver in the subtraction hybridization stage as described below, it is essential that the cDNA produced should be substantially wholly first strand cDNA since only the first strand cDNA can be subtracted. Second strand cDNA cannot be so subtracted as it would have no complementary counterpart in the subtracting driver mRNA utilised in this process, and hence an RNase H free reverse transcriptase enzyme should be used.

After completing the first strand cDNA synthesis, the RNA template strand was removed by alkaline hydrolysis (0.5M NaOH at 55° C. for 15 min.), and the first strand cDNA was recovered by ethanol precipitation following passage of the reaction mixture through a Sephadex G50 (Registered Trade Mark) spin column, prepared as described for example in Molecular Cloning: A Laboratory Manual, Maniatis, T., Fritsch, E. F. & Sambrook, J. (1982),—Cold Spring Harbor Publication ISBN 0-87969-136-0, p.466. The above-mentioned ethanol precipitation was accomplished by adding salt to a concentration of 0.1M, followed by adding three volumes of ethanol. The mixture was then cooled on dry ice for about 10 minutes, followed by centifugation in a bench top microcentrifuge for 10 minutes at 13,000 rpm.

(b) Subtractive Hybridization

Approximately 500 ng of the first stand cDNA obtained in the last stage was then hybridized to excess DNA free Poly $A^+$ mRNA (10 µg) isolated (as previously described) from the normal RJKO cells (reference cell source) that do not express the $O^6$-MMT gene, i.e. not subjected to the treatment with mitozolamide. In general, a 5–50 fold excess of this driver mRNA over the mRNA from the target cell source should be used for this hybridization.

The hybridization was carried out for approximately 20 hours at 68° C. in a total volume of 10 µl containing 0.5M NaCl, 25 mM hepes buffer (pH 7.5), 5 mM EDTA (ethylenediaminetetraacetic acid) and 1% SDS (sodium dodecylsuphate). This mixture was then diluted five fold with sterile distilled water, and the RNA-cDNA complex was precipitated by the addition of three volumes of ethanol. The precipitate, containing the cDNA-RNA duplex hybrids and free low abundance unsubtracted single strand cDNA, was dissolved in 50 µl of 25 mM Tris-HCl (pH 7), 1 mM EDTA, 5% DMSO (dimethylsulphoxide), together with 2 mM ascorbic acid, and was incubated at 68° C. for 3 minutes to remove hairpin structures from the single stranded cDNA.

The incubation temperature was then lowered to 45° C. and 2,5-diaziridinyl-1,4-benzoquinone (DZQ) in fresh dry DMSO was added to a relatively high concentration of 200 µM. Still at neutral pH, the reaction mixture was left for 20 minutes at the same temperature, a time sufficient under the reducing conditions produced by the ascorbic acid for GC base pairs of the RNA-cDNA hybrids to become effectively chemically cross-linked by the DZQ. The nucleic acid material containing the unsubtracted cDNA product was then precipitated (three vols. ethanol, 0.1 vol. 3M sodium acetate) and, optionally, a second round of hybridization was carried out following addition of a further 10 µg of DNA free Poly $A^+$ mRNA from the untreated RJKO cells. This rehybridization stage was carried out as before, again for 20 hours, as above described.

(c) Radiolabelling

The subtracted probe was produced by a second strand synthesis and labelling operation carried out, still in the presence of the RNA-cDNA duplex hybrids, directly on the unsubtracted cDNA product (i.e. substantially wholly single stranded cDNA unique to the treated RKJO cells) which provided a template, using random priming with a mixture of all possible hexanucleotides as the primer mixture and incubating in the presence of a mixture of deoxynucleoside triphosphates, including 100 µCi of $[\alpha^{32}P]$ dCTP, 3000 Ci/mMol, with 6 units of Sequenase II DNA polymerase substantially as recommended by the manufacturers. The incubation was carried out for 20 minutes at room temperature before terminating the reaction (e.g. by adding EDTA), and the product was then denatured by boiling to release the single stranded labelled DNA material for use as a probe. As previously indicated, use of the Sequenase DNA polymerase, rather than say Klenow fragment DNA polymerase, was important for the selective radiolabelling herein described. This is because the Sequenase DNA polymerase lacks any exonuclease activity and, most importantly, is unable to utilise RNA (e.g. in the cross-linked duplexes) as a template during the radiolabelling.

In general, it was not necessary to remove unincorporated deoxynucleoside triphosphates or surplus driver RNA remaining in the reaction mixture.

Figure 1B:
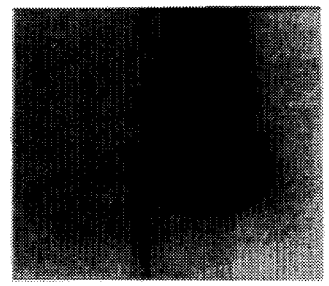

Results For testing, subtracted probes thus produced were applied in conjunction with Southern blotting to electrophoresed samples of α-actin and $O^6$-MMT cDNA cloning vector inserts (α-actin insert obtained from plasmid 91 described by Minty, A. J. et al. (1981) *J. Biol. Chem.* 256, 1008–1014, and the $O^6$-MMT insert obtained from the 1.1 Kb clone described by Rafferty, J. A. et al. (1992) *Nucleic Acids Research* 20, 1891–1895). The results of the Southern blotting on preparations of equal quantities (100 ng) of these inserts using a subtracted probe (produced after only one cycle of subtraction hybridization) and, for comparison, using an unsubtracted probe (made with the same amount of cDNA), are seen in the autoradiographs reproduced in FIG. 1 in the accompanying drawing. Using autoradiograph densitometry (performed by video image analyser, U.V. Products Version II, Cambridge, U.K.), the results of using the unsubtracted probe (B) show that the α-actin gene had an observed signal approximately 120–150 fold higher than that from the $O^6$-MMT level of expression. In contrast, the results of using the subtracted probe (A) show that the α-actin signal had been reduced to half that of the $O^6$-MMT gene cDNA which was maintained and indicated an overall enrichment of 240–300 fold in the relative response from the $O^6$-MMT gene after only one round of subtraction hybridization.

As already indicated, major advantages of this chemical cross-linking subtraction hybridization technique applied to the production of probes as herein above described include the fact that:

1) the subtracted probe does not need to be radiolabelled until use, thereby reducing manipulation of labelled DNA and also probe decay during the subtractive hybridization;

2) more than one probe preparation can be made from one batch of subtracted material;

3) the technique does not necessarily include physical separation of cDNA-RNA hybrids from unique cDNA's thereby improving efficiency and reducing losses of material that occur as a consequence of the extra manipulation necessary with other procedures.

A possible disadvantage of the technique may appear to reside in the fact that it requires at least 10 µg of poly $A^+$ mRNA, at least from the reference cell source when using this mRNA directly as the subtraction hybridization driver. This could be a limiting factor for some applications. However, this apparent disadvantage can be overcome if need be by generating an additional quantity of equivalent RNA through use of a directional cloning vector such as the lambda phage cDNA cloning vector described by Pallazzolo & Meyerowitz (1987) *Gene* 52, 197, whereby sense or antisense RNA can be synthesised from a cDNA population.

For constructing such a vector, an initial synthesis of double stranded cDNA from the cell mRNA source is carried out using a primer adapter, e.g. 5' XbaITTT 3', so that all the cDNA's have a restriction enzyme site (XbaI in the quoted example) at the 5' end. After methylation with a DNA methylase if necessary to protect against linker site cleavage, linkers providing a further restriction enzyme site (e.g. EcoRI) are ligated to the ends. Opposite ends of the cDNA molecules may then be selectively cleaved to permit ligation into the appropriately cut phage vector intermediate different RNA polymerase initiator promoter sites (e.g. SP6 and T7 of the lambda phage) on either side of the insert cloning site. One or other of these polymerase initiator promoter sites may then be selectively removed by restriction site digestion, allowing the other to be used to synthesize sense or antisense cDNA by in vitro transcription, all as described in the above-mentioned paper by Palazzolo and Meyerowitz of which the content is incorporation herein by reference.

The invention also includes all novel and inventive features and aspects herein disclosed, either explicitly or implicitly and either singly or in combination with one another, and the invention is not to be construed as being limited by the illustrative examples or by the terms and expressions used herein merely in a descriptive or explanatory sense, it being recognised that the scope of protection is defined and limited only by the claims which follow. In particular, it must also be pointed out that insofar as the terms "target cell source" and "reference (cell) source" are used in the present specification in the context of denoting abnormal tissue cells and normal tissue cells respectively, on the assumption that the abnormal tissue cells are expressing genes not expressed in the normal tissue cells, in some cases abnormal tissue cells may be characterised by a failure to express genes that are expressed by the normal tissue cells. In this event, in carrying out the invention, the normal tissue cells should therefore be regarded as being the "target cell source" and the abnormal tissue cells would be regarded as being the "reference cell source" from which the subtraction hybridization driver nucleic acid would be derived.

What we claim is:

1. In a subtraction hybridization process wherein single stranded cDNA derived from transcript RNA of a target cell source is reacted under hybridizing conditions with excess single stranded hybridization driver nucleic acid derived from transcript RNA of a reference source so as to cause substantially all said cDNA having a nucleotide sequence complementary to RNA that is common to both said sources to become bound in duplex molecules whereby the only single stranded cDNA then remaining is that having a sequence complementary to transcript RNA that is specific to the target cell source, that is, unique cDNA derived solely from said target cell source, the improvement which comprises the step of treating the reaction mixture with an aziridinylbenzoquinone interstrand cross-linking agent effective selectively to chemically cross-link the nucleotide strands in the duplex molecules, thereby increasing the stability of these molecules, without affecting the remaining unsubtracted single stranded cDNA; and subsequently subjecting the unsubtracted single stranded unique cDNA to random primed labelling in the presence of the chemically cross-linked duplex molecules, using a DNA polymerase lacking exonuclease activity and inactive with respect to said duplex molecules, thereby synthesizing labeled DNA strands complementary to said single stranded unique cDNA, and recovering the labeled product in a form usable as a hybridization probe for detecting a nucleotide sequence of that gene or genes of the target cell source responsible for producing said transcript RNA specific to the target cell source.

2. The process claimed in claim 1, wherein the labelling is carried out using a radioactive labelling agent.

3. In a subtraction hybridization process wherein single stranded cDNA derived from transcript RNA of a target cell source is reacted under hybridizing conditions with excess single stranded hybridization driver nucleic acid derived from transcript RNA of a reference source so as to cause substantially all said cDNA having a nucleotide sequence complementary to RNA that is common to both said sources to become bound in duplex molecules whereby the only single stranded cDNA then remaining is that having a sequence complementary to transcript RNA that is specific to the target cell source, that is, unique cDNA derived solely from said target cell source, the improvement which comprises the step of treating the reaction mixture with an aziridinylbenzoquinone interstrand cross-linking agent effective selectively to chemically cross-link the nucleotide strands in the duplex molecules, thereby increasing the stability of these molecules, without affecting the remaining unsubtracted single stranded cDNA; and subsequently cloning the unsubtracted single stranded unique cDNA in the presence of the chemically cross-linked duplex molecules using an appropriate vector and transformant host cells for providing a cDNA subtraction library.

4. The process claimed in claim 1 or 3, wherein the aziridinylbenzoquinone cross-linking agent is a compound of the formula

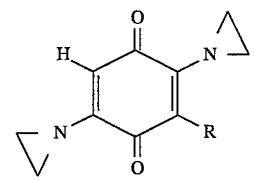

in which R is selected from H, alkyl, thiol, alcohol and halide.

5. The process claimed in claim 1 or 3, wherein the aziridinylbenzoquinone cross-linking agent is 2,5-diaziridinyl-1,4-benzoquinone (DZQ).

6. The process of claim 3 including, for use in constructing said vector, a step of converting the unsubtracted single stranded unique cDNA into a double stranded form by means of at least one stage of second strand synthesis using random priming.

7. In a subtraction hybridization process wherein single stranded cDNA derived from mRNA of a target cell source is reacted under hybridizing conditions with excess hybridization driver mRNA from a reference tissue cell source to cause substantially all said cDNA having a nucleotide sequence complementary to mRNA that is common to both said sources to become bound in RNA/DNA duplex molecules, leaving in single stranded form all cDNA having a sequence complementary to mRNA that is specific to the target cell source, that is, unique cDNA derived solely from said target cell source, the improvement which comprises the step of treating the reaction mixture with an aziridinylbenzoquinone interstrand cross-linking agent effective selectively to chemically cross-link the RNA and cDNA strands in the RNA/DNA duplex molecules, followed by the step of subjecting the unsubtracted single stranded unique cDNA to a random primed second strand synthesis operation in the presence of the chemically cross-linked RNA/DNA duplex molecules, using a DNA polymerase lacking exonuclease activity and inactive with respect to said RNA/DNA duplex molecules, thereby synthesizing only DNA strands complementary to said single stranded unique cDNA.

8. The process of claim 7 in which said second strand synthesis operation is carried out using a labelled deoxynucleotide compound so that the DNA strands synthesised are also labelled, said process including the further step of recovering the labelled product in a form usable as a hybridization probe for detecting a nucleotide sequence of that gene or genes of the target cell source responsible for producing said mRNA specific to the target cell source.

9. The process of claim 7 or 8, wherein the aziridinylbenzoquinone cross-linking agent is a compound of the formula

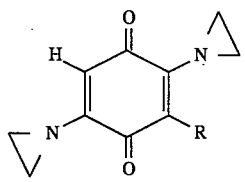

in which R is selected from H, alkyl, thiol, alcohol and halide.

10. A process for producing DNA hybridization probes of high specific activity from target tissue cells having genes that are differentially expressed as compared with the genes of reference tissue cells, which process comprises:

(a) making a preparation of mRNA derived from a sample of said target tissue cells:

(b) making a preparation of mRNA derived from a sample of said reference tissue cells;

(c) synthesizing first strand cDNA from said target tissue cell derived mRNA;

(d) mixing said first strand cDNA from step (c) with excess reference tissue cell derived mRNA from step (b) under hybridizing conditions in a subtraction hybridization process whereby such cDNA as is derived from genes that are expressed in both the target tissue cells and the reference tissue cells, and which is therefore complementary to mRNA from step (b), becomes bound in RNA/DNA duplexes so that the only single stranded cDNA remaining in the reaction mixture is then the unique cDNA that is derived from genes expressed solely in the target tissue cells;

(e) treating the reaction mixture with an aziridinylbenzoquinone interstrand cross-linking agent effective selectively to chemically cross-link the nucleotide strands in the RNA/DNA duplex molecules;

(f) synthesizing from said first strand unique cDNA a complementary labelled second strand cDNA by means of a random priming method carried out in the presence of said chemically cross-linked RNA/DNA duplex molecules using a random oligonucleotide primer mixture including at least one labelled deoxynucleoside triphosphate and a DNA polymerase which lacks exonuclease activity and which is inactive with respect to said RNA/DNA duplexes;

(g) denaturing as required to provide the labelled product in a single stranded form suitable for use as a DNA probe.

11. The process of claim 10 wherein a radiolabelled deoxynucleoside triphosphate is used in step (f).

12. The process of claim 11 wherein the mixture obtained after step (e) is stored at low temperature and step (f) is deferred until the probe is required for use.

13. The process of claim 10 wherein the aziridinylbenzoquinone cross-linking agent is a compound of the formula

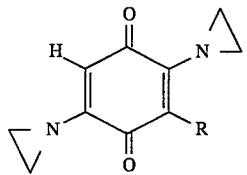

in which R is selected from H, alkyl, thiol, alcohol and halide.

14. The process of claim 10 wherein the aziridinylbenzoquinone cross-linking agent is 2,5-diaziridinyl-1,4-benzoquinone (DZQ).

15. The process of claim 10, wherein step (f) is carried out while the unsubtracted unique cDNA and the cross-linked duplex molecules are all immobilised on a solid phase support.

16. The process of claim 14, wherein the first strand cDNA is synthesized in step (c) using a biotinylated primer, and said solid phase support comprising solid material having a coating selected from avidin and streptavidin is introduced into the reaction mixture after step (e).

17. The process of claim 16, wherein said solid phase support comprises (strept)avidin coated magnetic beads or microspheres.

* * * * *